United States Patent [19]

Uchida et al.

[11] Patent Number: 5,061,730
[45] Date of Patent: Oct. 29, 1991

[54] CARBOXYLIC ACID DERIVATIVES

[75] Inventors: Itsuo Uchida; Hiroshi Hatanaka; Kumiko Nitta; Seiji Hashimoto; Masakuni Okuhara; Hidetsugu Murai; Masashi Hashimoto, all of Tsukuba, Japan

[73] Assignee: Fujisawa Pharmaceutical Co., Ltd., Osaka, Japan

[21] Appl. No.: 143,942

[22] Filed: Jan. 14, 1988

[30] Foreign Application Priority Data

Jan. 26, 1987 [GB] United Kingdom ............... 8701618
Jul. 7, 1987 [GB] United Kingdom ............... 8715931

[51] Int. Cl.$^5$ ............... C07C 259/06; A61K 31/19
[52] U.S. Cl. ............... 514/563; 435/128; 562/444; 562/568; 514/210
[58] Field of Search ............... 562/444, 568; 514/563, 514/210

[56] References Cited

U.S. PATENT DOCUMENTS 4,757,066 7/1988 Shiokari et al. ............... 514/210

FOREIGN PATENT DOCUMENTS 48301 3/1982 European Pat. Off. ............ 514/210
1272553 10/1989 Japan ............... 562/568

Primary Examiner—Carolyn Elmore
Attorney, Agent, or Firm—Oblon, Spivak, McClelland, Maier & Neustadt

[57] ABSTRACT

This invention relates to new carboxylic acid derivatives of the formula:

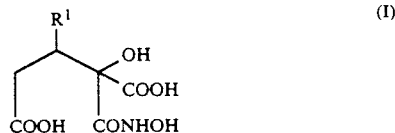

wherein $R^1$ is hydrogen, lower alkyl or aryl, and pharmaceutically acceptable salt thereof which inhibit activity of DHP-I, to a process for preparing them and to an antibacterial composition comprising them and carbapenem antibiotics.

5 Claims, No Drawings

CARBOXYLIC ACID DERIVATIVES

This invention relates to new carboxylic acid derivatives. More particularly, it relates to new carboxylic acid derivatives which inhibit activity of dehydropeptidase-I [DHP-I, renal dipeptidase (E.C. 3.4.13.11)] and therefore are useful as DHP-I inhibitors for preventing unnecessary hydrolysis of the β-lactam ring of carbapenem antibiotics by DHP-I in animal or human bodies, to a process for preparing them and to an antibacterial composition comprising the carboxylic acid derivatives and carbapenem antibiotics.

The carboxylic acid derivatives of this invention can be represented by the following formula:

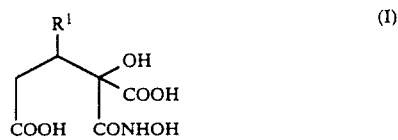

(I)

wherein $R^1$ is hydrogen, lower alkyl or aryl.

The pharmaceutically acceptable salt of the compound (I) may include a salt with an inorganic or organic base such as an alkali or alkaline earth metal salt (e.g. sodium salt, potassium salt, calcium salt, etc.) and a salt with an amino acid (e.g. arginine, etc.).

As DHP-I inhibitors, for example, cilastatin has already been known for improving urinary recoveries of the carbapenem antibiotics (e.g. imipenem) and is widely used for the therapeutical purpose of various infectious diseases [Cf. The American Journal of Medicine, 3, 14, 78 (suppl 6A), June 7, 1985].

The inventors of this invention has succeeded in isolating new DHP-I inhibitors from the cultured broth of a newly-isolated microorganism, *Streptomyces* sp. No. 1358 in the result of various investigations.

The new DHP-I inhibitors thus obtained (code names: WS-1358 A and WS-1358 B) have the following physicochemical properties.

| WS-1358A (as its disodium salt) | |
|---|---|
| (1) Appearance: | Colorless Powder |
| (2) Molecular Weight: | m/z 266 (M + H) [SI-MS (positive)] |
| (3) Elementary analysis: | |
| Found | C, 30.05; H, 3.84; N, 4.88; Na, 15.89% |
| Calcd for $C_7H_9NO_7Na_2.H_2O$ | |
| | C, 29.69; H, 3.92; N, 4.95; Na, 16.24% |
| (4) Melting point: | 98–100° C. (dec) |
| (5) Specific Rotation: | $[\alpha]_D^{23} = -14°$ (C = 0.9, $H_2O$) |
| (6) UV Spectrum: | End absorption ($H_2O$, pH 2 and 7), $\lambda_{max}$ = 228 nm ($H_2O$, pH11) |
| (7) IR Spectrum: | 3500–2500, 1660, 1580, 1360, 1160, 1100, 1000, 880, 800 $cm^{-1}$ (KBr) |
| (8) $^1$H-NMR Spectrum (400 MHz, $D_2O$) | |
| δ: 2.77 (1H, m), 2.18 (1H, dd, J=13.5 and 3Hz), 1.96 (1H, dd, J=13.5 and 11Hz), 0.82 (3H, d, J=6.5Hz) | |
| (9) $^{13}$C-NMR Spectrum (100 MHz, $D_2O$) | |
| δ: 184.7(s), 177.7(s), 173.2(s), 86.0(s), 42.2(t), 38.9(d), 15.8(q) | |
| (10) Solubility Soluble: | Water |
| Sparingly Soluble: | Methanol, Ethanol |
| Insoluble: | Acetone, Ethyl acetate, Chloroform, Hexane |
| (11) Color Reaction: Positive: | Ferric Chloride, Ehrlich, Ninhydrin, Iodine vaper |
| Negative: | Dragendorff, Molish, Cerium sulfate |
| (12) Rf value: iso-propanol:water (65:35) | 0.56 |
| iso-propanol:water:acetic acid (65:25:10) | 0.58 |
| n-butanol:acetic acid:water (2:1:1) | 0.43 |
| [on Silica Gel 60 Plate $F_{254}$ (Merck)] | |

| WS-1358B (as its disodium salt) | |
|---|---|
| (1) Appearance: | Colorless Powder |
| (2) Molecular Weight: | m/z 250 (M − H)[SI-MS(negative)] |
| (3) Elementary analysis: | |
| Found | C, 27.39; H, 2.91; N, 5.26; Na, 17.02 |
| Calcd for $C_6H_7NO_7Na_2.2/3H_2O$ | |
| | C, 27.39; H, 3.19; N, 5.32; Na, 17.50 |
| (4) Melting point: | 92–93° C. (dec) |
| (5) Specific rotation: | $[\alpha]_D^{23} = +2.5°$ (C = 1.0, $H_2O$) |
| (6) UV Spectrum: | End absorption ($H_2O$, pH 7), $\lambda_{max}$ = 225 nm ($H_2O$, pH = 11) |
| (7) IR Spectrum: | 3500–2500, 1660, 1620, 1580, 1400, 1380, 1200, 1130, 1100, 880, 800 $cm^{-1}$ (KBr) |
| (8) $^1$H-NMR Spectrum (400 MHz, $D_2O$) | |
| δ: 2.25–2.11 (4H, m) | |
| (9) $^{13}$C-NMR Spectrum (100 MHz, $D_2O$) | |
| δ: 185.3(s), 178.2(s), 173.7(s), 82.7(s), 35.6(t), 34.8(t) | |
| (10) Solubility Soluble: | Water |
| Sparingly Soluble: | Methanol, Ethanol |
| Insoluble: | Acetone, Ethyl acetate, Chloroform, Hexane |
| (11) Color Reaction Positive: | Ferric chloride, Ehrlich, Ninhydrin, Iodine vapor |
| Negative: | Dragendorff, Molish, Cerium sulfate |
| (12) Rf Value iso-propanol:Water (65:35) | 0.46 |
| iso-propanol:water:acetic acid (65:25:10) | 0.52 |
| n-butanol:acetic acid:water (2:1:1) | 0.40 |
| [on Silica Gel 60 Plate $F_{254}$ (Merck)] | |

From the analysis of the above physical and chemical properties and the result of further investigations for identification of chemical structures, each of the chemical structures of the WS-1358A and WS-1358B have been identified and assigned as follows.

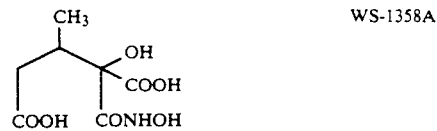

WS-1358A

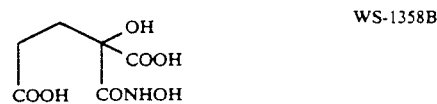

WS-1358B

The compound (I) can be prepared by fermentation and synthesis. Namely, the WS-1358 A and WS-1358B can be prepared by culturing a WS-1358 A and/or WS-1358B-producing strain belonging to the genus *Streptomyces* in a nutrient medium and recovering the WS-1358A and WS-1358B from the cultured broth.

Among a WS-1358A and/or WS-1358B-producing strain belonging to the genus *Streptomyces*, *Streptomyces* sp No. 1358 was newly isolated from a soil sample by inventors of this invention.

of the newly isolated *Streptomyces* sp. No.1358 have been deposited with one of the INTERNATIONAL DEPOSITORY AUTHORITY on the BUDAPEST TREATY, Fermentation Research Institute, Agency of Industrial Science and Technology at 1-3, Higashi 1 chome, Tsukuba-shi Ibaraki-ken 305, Japan since Jan. 9, 1987 and were assigned the deposit number FERM BP-1638(formerly FERM P-9120).

It is to be understood that the production of the WS-1358A and WS-1358B is not limited to the use of the particular organism described herein, which is given for illustrative purpose only. This invention also includes the use of any mutants which can be produced from the described organism by conventional means, such as X-rays, ultra-violet radiation, treatment with N-methyl-N'-nitro-N-nitrosoguanidine, 2-aminopurine and the like.

*Streptomyces* sp. No. 1358 has the following microbiological characteristics.

The strain No. 1358 was isolated from a soil sample collected at Tochigi City, Tochigi Prefecture, Japan. This organism belongs to the order *Actinomycetales* (Gram-positive, filamentous and branched bacteria). Its taxonomic characteristics are as follows. Morphological and cultural characteristics were observed on the various media described by Shirling and Gottlieb(1) after 7, 14 and 21 days of incubation at 30° C. The color descriptions used in this Spec. were based on the Methuen Handbook of Colour (2). Whole cell, mycolate and phospholipid compositions were determinated by methods described by Becker et al.(3) and Lechevalier and Lechevalier(4).

Substrate and aerial mycelia were well developed but did not fragment in agar media. The aerial mycelia bore the chains of 10 to 50 spores. These spore chains were non-verticillate, closely spiral, sometimes looped, and belonged in the section Spira. Spores were subglobose to oblong, smooth and 0.5–0.7×0.5–0.9 μm. These spore masses often appeared to coalesce in moist globules. Sclerotia, synnemata and sporangia were not observed.

Cultural characteristics on various agar media are shown in Table 1. The aerial mass color belonged in the Grey color series (pale grey, yellowish grey or brownish grey). Colony surface and reverse were yellowish white to greyish yellow. Melanoid and other soluble pigments were not produced.

Hydrolyzed whole cells of strain No. 1358 contained the LL-diaminopimelic acid (Becker's cell wall type I). Mycolic acid was absent. This strain had a type PII phospholipid pattern (diagnostic phospholipids were phosphatidylethanolamine).

Physiological properties of strain No. 1358 are presented in Table 2. This organism was an aerobic, mesophilic acid chromogenic bacterium. Its starch hydrolysis was strong, but protein hydrolysis was poor. The strain could utilize many carbon source for growth (Table 3).

Above-mentioned microscopic observation and cell analysis introduced that this strain belonged to the genus *Streptomyces* Waksman and Hendrici 1943. Then, we identified this strain as one strain of *Streptomyces* and named it to *Streptomyces* sp. No.1358.

Literature cited

1. Shirling, E. B., and D. Gottlieb. 1966. Methods for characterization of *Streptomyces* species. Int. N. Syst. Bacteriol. 16:313–340.
2. Kornerup, A., and J. H. Wanscher, 1978. Methuen Handbook of Colour, Methuen, London.
3. Becker, B., M. P. Lechevalier and H. A. Lechevalier, 1965. Chemical composition of cell wall preparations from strains of various form-genera of aerobic actinomycetes, Appl. Microbiol. 13:236–243.
4. Lechevalier, M. P. and H. A. Lechevalier, 1980. A university laboratory approach (emphasis on generic characterization), p.225–291. In A. Dietz and D. W. Thayer (ed), Actinomycete Taxonomy, SIM Spec. Publ. No.6, Soc. Ind. Microbial, Arlington.

TABLE 1

Cultural characteristics of the strain No. 1358.

| Medium | Cultural characteristics |
|---|---|
| Yeast extract-malt extract agar (ISP 2) | G: Good<br>AM: White, brownish grey (6D2), greyish brown (7F3)<br>R: Greyish yellow (4B3)<br>SP: None |
| Oatmeal agar (ISP 3) | G: Moderate<br>AM: Greyish brown (5F3)<br>R: Yellowish white (3A2)<br>SP: None |
| Inorganic salts-starch agar (ISP 4) | G: Good<br>AM: Brownish grey (7D-E2)<br>R: Greyish yellow (4B3)<br>SP: None |
| Glycerol-asparagine agar (ISP 5) | G: Good<br>AM: Orange grey (6C2)<br>R: Yellowish white (4A2)<br>SP: None |
| Peptone-yeast extract-iron agar (ISP 6) | G: Moderate<br>AM: None<br>R: Light yellow (4A4-5)<br>SP: None |
| Tyrosine agar (ISP 7) | G: Good<br>AM: Orange grey (5B2), brownish grey (7E2)<br>R: Greyish orange (5B3)<br>SP: Scant; greyish orange |
| Glucose-asparagine agar | G: Good<br>AM: Brownish grey (6C-D2), greyish brown (7F3)<br>R: Yellowish white (4A2)<br>SP: None |
| Nutrient agar | G: Moderate<br>AM: None<br>R: Pale yellow (3A3)<br>SP: None |
| Bennett agar | G: Good<br>AM: Dark brown (6F4)<br>R: Pale yellow (3A3)<br>SP: None |
| Sucrose-nitrate agar | G: Good<br>AM: None<br>R: Pale yellow (3A3)<br>SP: None |

G: Growth of substrate mycelium,
AM: aerial mycelium,
R: reverse,
SP: soluble pigment.

TABLE 2

Physiological properties of the strain No. 1358

| Test | Reaction |
|---|---|
| Temperature range for growth | 16–33° C. |
| Optimum temperature | 26–32° C. |
| Liquefaction of gelatin | Weakly positive |
| Coagulation of milk | Negative |
| Peptonization of milk | Weakly positive |
| Hydrolysis of starch | Positive |
| Melanoid production | Negative |
| Decomposition of cellulose | Negative |
| Nitrate reduction | Positive |
| NaCl tolerance | 0–2% |

TABLE 3

Utilization of carbon sources by the strain No. 1358.

| Carbon sources | Utilization |
|---|---|
| None | — |

TABLE 3-continued

| Utilization of carbon sources by the strain No. 1358. | |
|---|---|
| Carbon sources | Utilization |
| Glucose | ++ |
| L-Arabinose | ++ |
| D-Xylose | ++ |
| Inositol | ++ |
| Mannitol | ++ |
| D-Fructose | ++ |
| L-Rhamnose | ++ |
| Sucrose | ++ |
| Raffinose | ++ |

The WS-1358A and B can be produced by culturing a WS-1358A and/or B-producing strain belonging to the genus *Streptomyces* in a nutrient medium containing assimilable sources of carbon and nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed flour, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nitrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the WS-1358A and B.

For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the object compounds. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the object compounds.

Agitation and aeration of the culture mixture, may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced WS-1358A and B can be recovered from the culture medium by conventional means which are commonly used for the recovery of other fermentation products such as antibiotics.

In general, most of the WS-1358A and B produced are found in the culture filtrate, and accordingly the object compounds can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The WS-1358A and B can be separated each other and isolated, for example, by subjecting a crude material comprising WS-1358A and B to a column chromatography using a resin (e.g. Diaion SP-207, etc.).

The WS-1358A and B as obtained in their free forms may be converted to a salt with inorganic or organic base such as sodium salt, potassium salt, triethylamine salt and the like.

The compound (I) can also be prepared by the following synthetic processes.

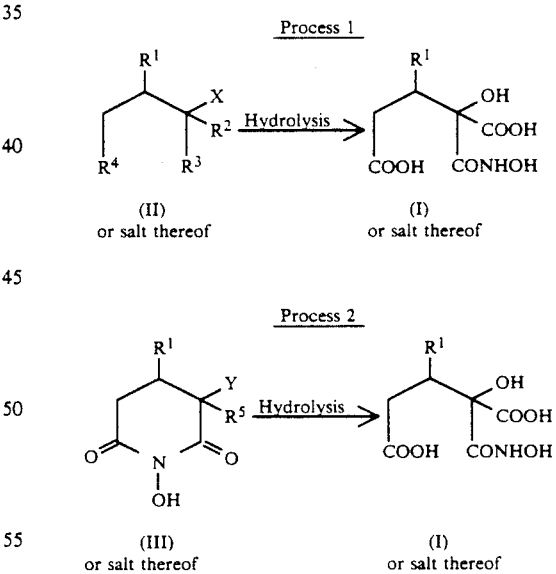

wherein
R$^1$ is the same as defined above,
R$^2$ and R$^3$ are each protected carboxy,
R$^4$ is hydroxycarbamoyl,
R$^5$ is carboxy or protected carboxy,
X is halogen and
Y is halogen or hydroxy.

The starting compounds (II) and (III) are novel compounds and can be prepared, for example, by the method specifically disclosed in the Examples or in a similar manner thereto.

The salts of the compounds (II) and (III) may include the same salt as exemplified in the explanation of the pharmaceutically acceptable salt of the compound (I).

In the above and subsequent descriptions of this specification, suitable examples and illustrations of the various definitions are explained in detail in the followings.

The term "lower" is intended to mean 1 to 6 carbon atom(s), unless otherwise indicated.

"Halogen" may include fluorine, chlorine, bromine and iodine.

Suitable "lower alkyl" may include methyl, ethyl, propyl, isopropyl, butyl, isobutyl, t-butyl, pentyl, hexyl and the like.

Suitable "aryl" may include aromatic hydrocarbon residue such as phenyl, tolyl, naphthyl and the like.

Suitable "protected carboxy" may include esterified carboxy such as lower alkoxycarbonyl (e.g. methoxycarbonyl, ethoxycarbonyl, propoxycarbonyl, etc.) and the like.

The processes as illustrated above are explained in more detail in the followings.

Process 1: Compound (II)→ Compound (I)
Process 2: Compound (III)→ Compound (I)

The compound (I) or salt thereof can be prepared by hydrolyzing the compound (II) or compound (III) or their salts.

The hydrolysis can preferably be carried out in the presence of inorganic or organic base (e.g. sodium hydroxide, etc.).

The reaction of this process is usually carried out in a solvent which does not adversely influence the reaction such as water, methanol, ethanol and the like at a temperature range of cooling to heating.

The object compound of the above processes 1-2 can be purified and converted to desired salts in a conventional manner.

The following tests are given for the purpose of illustrating biological property of the compound (I) of this invention.

In the tests, the following test compounds were used.

| Test compound No. | Formula |
|---|---|
| | (a) DHP inhibitors |
| 1 | CH₃, OH, COONa, COONa, CONHOH (as disodium salts of WS-1358 A) |
| 2 | OH, COONa, COONa, CONHOH (as disodium salts of WS-1358 B) |
| | (b) Carbapenem Antibiotics |
| 3 | [structure with OH, CH₃, COOH, S—CH₂CH₂NH—CH=NH] |
| 4 | [structure with OH, CH₃, COOH, S, NH, CH₂OCONH₂] |

TEST 1

(Inhibition of DHP-I activity)

DHP-I (renal dipeptidase) were partially purified from several species of animals by B. J. Cambell (Methods in Enzymology, (1970) Vol. 19,722). Fresh kidney cortex was cut into pieces and homogenized in a Waring blender with an equal volume of 1/15M phosphate buffer (pH 8.0). The homogenate was filtrated on gauze to remove cellular debris. n-Butanol chilled to 0° C., was added to a concentration of 20% by volume with rapid stirring. The suspension was stirred with a magnetic stirrer for overnight at 4° C. to dissolve DHP-I. The resultant emulsion was then dialyzed against several changes of distilled water. To the dialyzate was added solid ammonium sulfate to 50% saturation at 0° C. The precipitate formed was collected by centrifugation at 4500 g for 1 hour and discarded. Solid ammonium sulfate was then added to the supernatant to 75% saturation, the suspension was centrifuged at 10,000 g for 1 hour. The sediment was dissolved in a small volume of distilled water and dialyzed against distilled water. The dialyzate was used for enzyme assay.

Activity of DHP-I was measured by mean of using the unsaturated dipeptide, glycyldehydrophenylalanine as substrate. Enzymatic hydrolysis was followed by observing the fall in optical density at 275 nm. Inhibitory effect of the test compound on DHP-I activity was measured. Inhibition percent, I(%), was calculated as followed, $I(\%)=(E-T)/E \times 100$, where E was DHP-I activity without test compound (Control), T was DHP-I activity with test compound.

The results were shown in Table 4.

TABLE 4

| Source of DHP-I | IC$_{50}$ (ng/ml) | |
|---|---|---|
| | Test compound No. 1 | Test compound No. 2 |
| Porcine | 1.1 | 110 |
| Rabbit | 11 | 500 |

TEST 2

(Effect on other metalloenzymes)

DHP-I is a metalloenzyme with the zinc atom. To clarify the specific inhibitors activity of the test compound on DHP-I, the effect of the test compound on other metalloenzymes containing zinc, carboxypeptidaseA (CPaseA), leucineaminopeptidase (LAP), was determined.

Activity of CPaseA from bovine pancreas (Type II-DEF, made by Sigma Chemical Co.) was measured by mean of using carbobenzoxyglycyl-L-phenylalanine (made by Peptide Institute, Inc., Osaka, Japan) as substrate. Enzymatic hydrolysis was followed by observing the fall in optical density at 224 nm.

Activity of LAP from porcine kidney microsomes (Type IV-S, made by Sigma Chemical Co.) was measured by . mean of using L-leucine-p-nitroanilide (made by Peptide Institute, Inc.) as substrate. Enzymatic hydrolysis was followed by observing the increase in optical density at 405 nm.

The results shown that the test compounds No.1 and No.2 had no inhibitory effect on both enzymes at the concentration of 50,000 ng/ml.

TEST 3

(Antimicrobial activity)

Antimicrobial activity of the test compounds No.1 and No.2. was measured by paper disk diffusion method in a conventional manner. The results show that the test compounds No.1 and No.2 had no antimicrobial activity against microorganisms (*Staphylococcus aureus, Escherichia coli,* etc.) tested at the concentration of 1 mg/ml.

TEST 4

(Acute Toxicity)

The acute toxicity of the test compound No.1 was determined to ICR mice (female, 4 weeks old) by a single intravenous injection. No toxic symptom was observed at the dose of 1 g/kg.

TEST 5

(Effect on urinary recovery of carbapenem class of antibiotics)

The effect of the test compound No.1 on urinary recovery of carbapenem antibiotics simultaneously administrated was determined. Urinary recovery percent was calculated by measuring a quantity of antibiotics excreted in urine using bioassay, when antibiotics and DHP-I inhibitor were combined and intravenously injected to ICR mice (female, 4 weeks old, 4 animals per group).

The results are shown in Table 5. It made clear from the test results that the DHP-I inhibitor of this invention (test compound No. 1) significantly increased urinary recovery of the carbapenem antibiotics (test compound No.3 and 4: Dosage; 1 mg/kg).

TABLE 5

| Inhibitor | Urinary Recovery (%) | |
|---|---|---|
| | Test compound No. 3 | Test compound No. 4 |
| None | 44.1 ± 0.6 | 29.3 ± 2.8 |
| Test compound No. 1 | | |
| 0.5 mg/kg | 66.1 ± 3.0 | 51.4 ± 3.9 |
| 1 | 63.8 ± 7.3 | 57.8 ± 1.3 |
| 2 | 65.4 ± 9.5 | 71.9 ± 9.5 |

TEST 6

(Improved protective effect of carbapenem antibiotic combined with DHP-I inhibitor)

The combined effect of DHP-I inhibitor of this invention with the carbapenem antibiotic, on mice infection was determined. ICR mice (female, 4 weeks old, 5 animals per group) were intraperitoneally injected with $4 \times 10^8$ *Staphylococcus aureus* 47 suspended in 5% mucin. Combined therapies were administrated subcutaneously 1 hour after challenge.

The results are shown in Table 6 where the carbapenem antibiotic combined with the DHP-I inhibitor of this invention had improved protective effect on mice infection.

TABLE 6

| Test compound | Survived/Treated (Test mice) |
|---|---|
| Saline | 0/5 |
| Test compound No. 4 10 mg/kg | 0/5 |
| Test compound No. 4 10 mg/kg + Test compound No. 1 10 mg/kg | 4/5 |

As clear from the above test results, the compound (I) and pharmaceutically acceptable salt thereof have excellent inhibitory activity of DHP-I and are useful as DHP-I inhibitors for co-administering with the carbapenem antibiotic having the carbapenem nucleus of the formula:

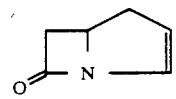

to human or animals in needs of antibiotic therapy.

The combination of the compound (I) or pharmaceutically acceptable salt thereof and the carbapenem antibiotic or pharmaceutically acceptable salt thereof can conveniently be administered to the human or animals in the form of an antibacterial composition containing the two components with pharmaceutically acceptable carrier(s). The combination ratio of the compound (I) or salt thereof and carbapenem antibiotic or salt thereof in the antibacterial composition may usually be selected within a range of 1:4 to 4:1 by weight, preferably 1:2 to 2:1 by weight and most preferably 1:1 by weight.

For applying the present antibacterial composition to human , it is preferable to apply it in the form of intravenous or intramuscular injection. It may also be applied locally in the form of a powder, a suppository or an ointment. When used as an injection, it may be applied in admixture with a solid or liquid carrier or diluent which is usually used for the conventional antibiotic injections, and further, may also be applied together with other medicines such as analgesics (e.g. lidocaine) which are usually used in injections. The most preferred carrier or diluent is water. When used as a suppository and an ointment, it may be used in admixture with conventional suppository and ointment bases, respectively.

For applying the present antibacterial composition to other animals. It is preferable to apply it in the form of injection or in the form of infusion. It may also be applied locally in a form cf a powder or an ointment.

When used as an injection or infusion, it may be applied in admixture with a solid or liquid carrier or diluent which is usually used for the conventional antibiotic injections or infusions. The most preferred carrier or diluent is water, vegitable oils, paraffins or the like. When used as an ointment, it may be applied in admixture with conventional ointment bases.

The dosage of the antibacterial composition may vary depending on various factors such as the weight and age of the patient, the kind and severity of the infection, and the kind of administration route. However, it is to be understood that, as the dosage of the effective ingredient included in the antibacterial composition, it may effectively be administered to the patient within a dosage range of 5-200 mg/kg/day, preferably 10-100 mg/kg/day. The total daily amount may divisionally given to the patient at the interval of 6 to 12 hours.

The following Example is given for the purpose of illustrating this invention.

EXAMPLE 1

An aqueous seed medium (160 ml) containing 1% of corn starch, 1% of glycerin, 0.5% of glucose, 1% of cotton-seed flour, 0.5% of dried yeast, 0.5% of corn steep liquor and 0.2% calcium carbonate (pH 6.5) was poured into each of sixty 500 ml Erlenmeyer flasks and sterilized at 120° C. for 30 minutes. A loopful of slant culture of *Streptomyces* sp. No.1358 was inoculated to each of the medium and cultured under shaking condition at 30° C. for 3 days.

An aqueous production medium (150 l) containing 1% of glucose, 2% of glycerin, 1% of cotton-seed flour, 1% of soy bean meal, 0.5% of dried yeast, 0.3% of calcium carbonate (pH 7.0) and 0.1% of Adekanol (defoaming agent, Trademark, made by Asahi Denka Co.) was poured into each of three 200 l-jar fermentors and sterilized at 120° C. for 30 minutes. The resultant seed culture broth (3.2 l) was inoculated to each of the production medium and cultured at 30° C. for 4 days, agitated at 250 rpm and aerated at 150 liters per minutes.

The cultured broth thus obtained (410 l) was filtered with the aid of diatomaseous earth (15 kg). The filtrate (390 l) was adjusted to pH 10 with 6N NaOH and allowed to stand for 2 hours at room temperature. The resultant precipitate was filtrated after addition of diatomaseous earth (3 kg) and discarded. The filtrate was passed through a column of an anion exchange resin, Dowex 1×2 (Cl-type, Trademark, made by Dow Chemical Co.) (13 l). The column was washed with water (38 l) and 0.1M NaCl, then eluted with 0.2M NaCl. The eluate (70.5 l) was adjusted to pH 1.8 with 6N HCl, passed through a column (16 l) of activated carbon (made by WAKO Pure Chemical Industries, Ltd.). The column was washed with water (48 l) and 25% aqueous methanol (48 l), eluted with 0.5N ammonium hydroxide containing 25% methanol. The eluate (32 l) was concentrated under reduced pressure to a volume of 950 ml and adjusted to pH 2 with 6N HCl. The resultant solution was applied on a column of a adsorption resin Diaion SP-207 (Trademark, made by Mitsubishi Chemical Industrials Ltd.) (5 l) equilibrated with water and developed with water. WS-1358B was eluted in fractions from 5 l to 7.5 l and WS-1358A was eluted in fractions from 8.5 l to 12.9 l.

ISOLATION OF WS-1358A

After the fraction containing WS-1358A thus obtained was concentrated under reduced pressure to a volume of 70 ml, an equal volume of 0.2M ammonium dihydrogen phosphate buffer (pH 23) was added to the residue. The resultant solution was passed through a column of an anion exchange resin, Dowex 1×2 (780 ml) equilibrated with 0.1M ammonium dihydrogen phosphate buffer (pH 2.3) and eluted with the same buffer. The continuous fraction from 5.2 l to 5.6 l containing WS-1358A was concentrated under reduced pressure and freeze-dried. The lyophilizate thus obtained was dissolved in deionized water (15 ml) and applied on a column of Diaion SP-207 (300 ml) equilibrated with water and developed with water. The active fraction from 1620 ml to 1900 ml was neutralized with 6N NaOH and applied on a column of Sephadex G-15 (Trademark, maker Pharmacia) (39 ml). The lyophilizate (35 mg) was obtained after the active fraction (3.9 ml) was freeze-dried. The lyophilizate was dissolved in 0.5N NaOH (3.5 ml) and allowed to stand for 30 minutes 15 at room temperature, then diluted to 15 ml with water after neutralization with 6N HCl. The resultant solution was applied on a column (10 ml) of DEAE-Sephadex A-25 (Cl-type, Trademark, made by Pharmacia) and eluted with water, 0.1M NaCl and 0.2M NaCl. The active fraction (50 ml) was adjusted to pH 2 with 6N HCl and concentrated under reduced pressure, then applied on a column of Diaion SP-207 (30 ml) and developed with water. The active fraction (9 ml)was adjusted to pH 7 with 1N NaOH and freeze-dried to give a white powder of disodium salt of WS-1358A (17 mg).

ISOLATION OF WS-1358B

The fraction (2.5 l) containing WS-1358B obtained by Diaion SP-207 column chromatography was neutralized with 1N NaOH and concentrated under reduced pressure. The resultant solution was applied on a column (780 ml) of Cellulose CF11 (Trademark, made by Whatman Co.) and washed with isopropanol (780 ml), then eluted with 75% aqueous isopropanol. The active fraction eluted from 2800 ml to 4600 ml was concentrated under reduced pressure and applied on a column of DEAE-Sephadex A-25 (Cl-type) (100 ml), then washed with water, 0.1M NaCl and eluted with 0.2M NaCl. The active fraction (350 ml) was concentrated to a volume of 15 ml under reduced pressure and applied on a column (3 l) of Sephadex G-15 equilibrated with water, then eluted with water. The active fraction containing WS-1358B was eluted from 1750 ml to 1910 ml. The resultant solution was concentrated under reduced pressure to give the residue. The residue was recrystalized from aqueous methanol to give colorless powder of disodium salt of WS-1358B (1.3 g).

EXAMPLE 2

(1) To a suspension of 60% sodium hydride in mineral oil (40 mg) in benzene (5 ml) was added a solution of diethyl 2-ethoxycarbonyl-3-methylglutarate (274 mg) in benzene (5 ml) with stirring. The mixture was stirred for 1 hour at 90° C. until light yellow solution was obtained. After cooled, to the resulting solution was added a solution of benzoyl peroxide (182 mg) in benzene at 0° C. over a period of 20 minutes. The mixture was stirred for 30 minutes at room temperature. The reaction mixture was poured into ice water and extracted with ether. The ether extract was washed with water, dried over magnesium sulfate and evaporated to give a residue (280 mg), which was chromatographed on silica gel, eluted with a mixture of ethyl acetate and hexane (10:90) to afford diethyl 2-benzoyloxy-2-ethoxycarbonyl 3-methyl-glutarate (250 mg) as an oil.

IR (CHCl$_3$, cm$^{-1}$): 2970, 1725, 1600, 1460, 1450, 1365, 1280, 1100, 1025, $^1$H NMR (CDCl$_3$) δ: 8.08 (2H, m), 7.67 to 7.42 (3H, m), 4.37 to 4.23 (4H, m), 4.17 (2H, q, J=7 Hz), 3.05 (1H, m), 2.81 (1H, dd, J=16, 3.5 Hz), 2.32 (1H, dd, J=16, 10 Hz), 1.34 to 1.23, (9H, m), 1.19 (3H, d, J=7 Hz).

(2) To a mixture of ethanol (0.4 ml) and water (0.4 ml) was added hydroxylamine hydrochloride (139 mg). To this solution was added 10N sodium hydroxide (0.4 ml) dropwise with stirring at 0° C. To the resulting solution was added a solution of diethyl 2-benzoyloxy-2-ethoxycarbonyl-3-methyl-glutarate (394 mg) in ethanol (2 ml), and the mixture was stirred for 3 hours at room temperature. The reaction mixture was acidified with 1N hydrochloric acid to pH2, and extracted with ether. The water layer was concentrated to remove ethanol and the pH of the water solution was adjusted to 2 with hydrochloric acid or 1N sodium hydroxide. The resulting solution was lyophilized. The lyophilizate was dissolved in water (4 ml) and applied on a column of non-ionic adsorption resin, Diaion SP-207 (trade mark, made by Mitsubishi Chemical Ind.) (20 ml) and developed with water. The fraction containing the objective compound was adjusted to pH 7 with 1N sodium hydroxide and freeze-dried to give sodium salt of 1,3-dihydroxy-4-methyl-2,6-dioxo-3-piperidine-carboxylic acid (15.3 mg) as a powder.

$^1$H-NMR (D$_2$O)δ 2.87 (1H, dd, J=17.5, 5 Hz), 2.75 (1H, dd, J=17.5, 9.5 Hz), 2.62 (1H, m), 0.98 (3H, d, J=7 Hz).

$^{13}$C-NMR (D$_2$O) 6 177.4, 174.2, 173.9 83.0, 38.6, 34.5, 15.9.

(3) Sodium salt of 1,3-dihydroxy-4-methyl-2,6-dioxo-3-piperidinecarboxylic acid (14 mg) was dissolved in 0.5N sodium hydroxide ( 2 ml) and allowed to stand for 30 minutes at room temperature, then diluted to 10 ml with water after neutralization with 6N hydrochloric acid. The resultant solution was applied on a column (6 ml) of DEAE-Sephadex A-25 (Cl-type, trademark, made by Pharmacia AB)and eluted with water, 0.05M, 0.1M and 0.2M aqueous sodium chloride. The active fraction (24 ml) was adjusted to pH2 with 6N hydrochloric acid and concentrated under reduced pressure, then applied on a column of non-ionic adsorption resin, Diaion SP-207 (trademark, made by Mitsubishi Chemical Industries) (18 ml) and developed with water. The active fraction was adjusted to PH7 with 1N sodium hydroxide and freeze-dried to give a white powder of disodium salt of 2-hydroxy-2-(hydroxycarbamoyl)-3-methylglutaric acid (7 mg)

$^1$H NMR (D$_2$O ), δ 2.77 (1H, m), 2.18 (1H, dd, J=13.5 and 3 Hz), 1.96 (1H, dd, J=13.5 and 11 Hz), 0.82 (3H, d, J=6.5 Hz).

$^{13}$C-NMR (D$_2$O): δ 6 184.7, 177.7, 173.2, 86.0, 42.2, 38.9, 15.8.

EXAMPLE 3

(1) 60 % Sodium hydride in mineral oil (0.2 g) was added to distilled benzene (30 ml) at room temperature under nitrogen atmosphere. To this suspension was added a solution of distilled diethyl malonate (8.16 g) in anhydrous benzene (30 ml) with stirring at same temperature. After the vigorous gas evolution deceased, a solution of benzyl crotonate (9 g) in anhydrous benzene (30 ml) was added under nitrogen atmosphere. The mixture was stirred at 90° C. overnight. After cooled, the reaction mixture was poured into ice water (200 ml) and benzene layer was separated. The water layer was extracted with ether (200 ml×2) and the ether layer was combined with the above separated benzene solution. The combined organic solution was washed with water (200 ml×2) and dried over magnesium sulfate. Removal of the solvent gave oily crude product (17 g), which was distilled under reduced pressure. Removal of the fractions of b.p. 50°-90° C./2 mm Hg afforded oily benzyl 4,4-bis(ethoxycarbonyl)-3-methylbutyrate (14.2 g) as a residue.

IR (CHCl$_3$) cm$^{-1}$: 1730, 1365, 1170, 1025.

$^1$H-NMR (CDCl$_3$): δ 7.35 (5H, m), 5.12 (2H, s), 4.19 (4H, q, J=7 Hz), 3.41 (1H, d, J=7 Hz), 2.75 (1H, m), 2.61 (1H, dd, J=16, 5 Hz), 2.37 (1H, dd, J=16, 8.5 Hz), 1.26 (6H, t, J=7 Hz), 1.08 (3H, d, J=7 Hz).

(2) To a solution of benzyl 4,4-bis(ethoxycarbony)-methylbutyrate (3.36 g) in dioxane (50 ml) was added 10% palladium on carbon (0.5 g). The mixture was hydrogenated at 5 atm. and at room temperature for 1 hour. The reaction mixture was filtered and the filtrate was concentrated to dryness under reduced pressure to give an oily residue (2.43 g), which was purified by silicagel column chromatography, eluted with a mixture of methanol and chloroform (5:95) to afford 4,4-bis-(ethoxycarbonyl)-3-methylbutyric acid (2.11 g) as an oil.

IR(CHCl$_3$) cm$^{-1}$: 3400-2500, 2960, 1720, 1365, 1300, 1175, 1155, 1030.

$^1$H-NMR (CDCl$_3$) δ 4.21 (4H, q, J=7 Hz), 3.42 (1H, d, J=7 Hz), 2.76 (1H, m), 2.64 (1H, dd, J=16, 5 Hz), 2.38 (1H, dd, J=16, 8.5 Hz), 1.28 (6H, t, J=7 Hz), 1.11 (3H, d, J=7 Hz).

(3) 4,4-bis(Ethoxycarbonyl)-3-methylbutyric acid (3.69 g) was dissolved in water (50 ml) with stirring, To this solution was added sodium hypochlorite solution (Wako Pure Chemical Industries, Ltd. available chlorine: min 5%, ca 25 ml), while slowly stirring the solution during a 30 minute period until the pH rose to 7.0. After the mixture was stirred further 30 minutes the reaction mixture was acidified to pH2 by addition of 1N hydrochloric acid and then extracted with ether (100 ml×3). The ether extract was washed with water (100 ml) and evaporated to give a residue (4.33 g), which was purified by silica gel column chromatography, eluted with a mixture of methanol and chloroform (5:95) to afford 4-chloro-4,4-bis(ethoxycarbonyl)-3methylbutyric acid (3.56 g) as an oil.

IR (CHCl$_3$, cm$^{-1}$): 3200-2500, 2970, 1740, 1710, 1300, 1250, 1095, 1080, 1040.

$^1$H NMR (CDCl$_3$) δ 6 4.30 (2H, q, J=7 Hz), 4.28 (2H, q, J=7 Hz), 3.14 (1H, m), 2.87 (1H, dd, J=16.5, 2.5 Hz), 2.33 (1H, dd, J=16.5, 10 Hz), 1.31 (3H, t, J=7 Hz), 1.29 (3H, t, J=7 Hz), 1.12 (3H, d, J=7 Hz).

(4) To a solution of 4-chloro-4,4-bis(ethoxycarbonyl)-3-methylbutyric acid (2.81 g) in dichloromethane (50 ml) was added N-hydroxysuccinimide (1.15 g) and the mixture was stirred at room temperature for 1 hour. To the resulting solution was added dicyclohexyl carbodiimide (2.06 g) at 0° C. and the mixture was stirred at 0° C. for 10 minutes, and then at room temperature overnight. The reaction mixture was filtered, and the filtrate was concentrated to dryness under reduced pressure to give 4-chloro-4,4-bis(ethoxycarbonyl)-3-methylbutyric acid succinimide ester (2.96 g) as an oil.

$^1$H-NMR (CDCl$_3$): δ 6 4.30 (2H, q, J=7 Hz), 4.29 (2H, q, J=7 Hz), 3.13 (1H, m), 3.10 (1H, dd, J=16.5, 2.5 Hz), 2.85 (4H, s), 2.59 (1H, dd, J=16.5, 10 Hz), 1.30

(3H, t, J=7 Hz), 1.29(3H, t, J=7 Hz), 1.15 (3H, d, J=7 Hz).

(5) To a solution of hydroxylamine hydrochloride (834 mg) in water (10 ml) was added 1N sodium hydroxide (15 ml) at 0° C. with stirring. The resulting solution was added to a solution of 4-chloro-4,4-bis(ethoxycarbonyl)-3-methylbutyric acid succinimide ester (2.96 g) in ethanol (30 ml) at 0° C. The mixture was stirred at room temperature for 5 hours. A trace of solid N,N-dicyclohexylurea of the reaction mixture was filtered off and the pH of the filtrate was adjusted to 6.5 by adding 1N hydrochloric acid or 1N sodium hydroxide. The resulting solution was stirred at 80° C. for hours and the cooled solution was acidified with 1N hydrochloric acid to pH2, and then diluted with water to a volume of 150 ml. The resulting solution was extracted with ethyl acetate (150 ml×3) and the extract was washed with water (150 ml), dried over magnesium sulfate and then evaporated to give a residue (2.7 g), which was chromatographed on silica gel column, eluted with a mixture of methanol and chloroform (5!95) to afford a mixture (ca 1:1) of diethyl 2-chloro-2-[(2-hydroxycarbamoyl-1-methyl)ethyl]malonate and ethyl 3-chloro-1-hydroxy-4-methyl-2,6-dioxo-3-piperidinecarboxylate (1.78 g) as an oil. 100 mg of this oil was subjected to preparative thin layer chromatography [silicagel plate, developed with a mixture of isopropanol and benzene (10:90)] to give diethyl 2-chloro-2-[(2-hydroxycarbamoyl-1-methyl) ethyl]malonate A, 44 mg), and ethyl 3-chloro-1-hydroxy-4-methyl-2,6-dioxo-3-piperidine-carboxylate (B, 45 mg) as oils.

| A, IR(CHCl$_3$, cm$^{-1}$): | 3450, 3200, 2980, 1740, 1665, 1460, 1385, 1365, 1295, 1255, 1095, 1035 |
|---|---|
| $^1$H NMR (CD$_3$OD): δ | 4.28 (4H, q, J=7Hz), 3.10 (1H, m), 2.47 (1H, dd, J=2.5, 14Hz), 2.03 (1H, dd, J=11, 14Hz), 1.29 (6H, t, J=7Hz), 1.04 (3H, d, J=7Hz). |
| $^{13}$C NMR (CD$_3$OD): δ | 170.5, 167.4, 167.3, 76.8, 64.2, 64.2, 38.0, 36.5, 15.4, 14.2, 14.2 |
| B IR (CHCl$_3$, cm$^{-1}$): | 3350, 3030, 3000, 2950, 1750, 1695, 1460, 1390, 1370, 1260, 1080, 1020, 875, 835 |
| $^1$H NMR (CD$_3$OD): δ | 4.35 (2H, q, J=7Hz), 3.11 (1H, m), 2.82 (2H, m), 1.31 (3H, t, J=7Hz), 1.04 (3H, d, J=7Hz). |
| $^{13}$C NMR (CD$_3$OD): δ | 168.2, 166.3, 165.3, 75.2, 64.9, 37.1, 34.0, 14.7, 14.2 |

(6) To a mixture of diethyl 2-chloro-2-[(2-hydroxycarbamoyl-1-methyl)-ethyl]-malonate and ethyl 3-chloro-1-hydroxy-4-methyl-2,6-dioxo-3-piperidine-carboxylate (1:1, 80 mg) was added 1N sodium hydroxide (3 ml), and the resulting mixture was stirred for 3 hours at room temperature and then neutralized with 1N hydrochloric acid. Thus obtained solution was subjected to high performance liquid chromatography (HPLC, column: Toyo-Soda, TSK gel ODS, 80 TM, 4 φ×150 mm; mobile phase: 0.2M NH$_4$.H$_2$PO$_4$. pH4; detection: 210 nm UV detector). The HPLC showed the major peak (retention time: 5.52 min.) of the product was identical with that of natural product, disodium salts of WS-1358A, disodium salts of 2-hydroxy-2-(hydroxycarbamoyl)-3-methylglutaric acid and the yield was 70%. The reaction mixture was concentrated under reduced pressure to dryness to give a residue containing disodium salts of 2-hydroxy-2-(hydroxycarbamoyl)-3-methylglutaric acid, $^1$H and $^{13}$C NMR of which showed the major signals were identical with those of disodium salts of WS-1358 A.

$^1$H-NMR (D$_2$O): δ 6 2.77 (1H, m), 2.18 (1H, dd, J=13.5, 3 Hz), 1.96 (1H, dd, J=13.5, 11Hz), 0.82 (3H, d, J=6.5 Hz).

$^{13}$C-NMR (D$^2$O): δ 6 184.7,177.7, 173.2, 86.0, 42.2, 38.9, 15.8.

(7) 70% purity of disodium salts of 2-hydroxy-2-(hydroxycarbamoyl)-3-methylglutaric acid which was obtained in the previous reaction, was dissolved in water (3 ml) and the solution was acidified with 6N hydrochloric acid to pH 1.6 and then lyophilized. The lyophilizate was dissolved in water (1.2 ml) and applied on a column of nonionic adsorption resin, Diaion SP-207 (trademark, made by Mitsubishi Chemical Industries) (20 ml) equilibrated with water and developed with water. The fraction containing the objective compound was adjusted to pH 6.8 to 7.0 with 1N sodium hydroxide and freeze-dried to give sodium salt of 1,3-dihydroxy-4-methyl-2,6-dioxo-3-piperidinecarboxylic acid (18 mg) as a powder.

$^1$H NMR (D$_2$O): δ 6 2.87 (1H, dd, J=17.5, 5 Hz), 2.75 (1H, dd, J=17.5, 9.5 Hz), 2.62 (1H, m), 0.98 (3H, d, J=7 Hz).

$^{13}$C NMR (D$_2$O): δ 6 177.4, 174.2, 173.9, 83.0, 38.6, 34.5, 15.9.

(8)To diethyl 2-chloro-2-[(2-hydroxycarbamoyl-1methyl)ethyl]malonate (30 mg) was added 1N NaOH (1 ml) and the resulting mixture was stirred for 5 hours at room temperature. The reaction mixture was neutralized with 1N hydrochloric acid, and the solution was subjected to HPLC, which showed the major peak of the product was identical with that of natural product, WS-1358A, 2-hydroxy-2-(hydroxycarbamoyl)-3-methylglutaric acid and the yield was 74%. The solution was concentrated under reduced pressure to dryness to give a crude product containing disodium salt of 2-hydroxy-2-(hydroxycarbamoyl)-3-methylglutaric acid, $^1$H-NMR of which showed the major signals were identical with those of disodium salts of WS-1358A.

$^1$H NMR (200 MHz, D$_2$O): δ 6 2.77 (1H, m), 2.18 (1H, dd, J=13.5, 3 Hz), 1.96 (1H, dd, J=13.5, 11 Hz), 0.82 (3H, d, J=6.5 Hz).

(9) To ethyl 3-chloro-1-hydroxy-4-methyl-2,6-dioxo-3-piperidinecarboxylate (25 mg) was added 1N sodium hydroxide (1 ml), and the mixture was stirred for 5 hours at room temperature, and then neutralized with 1N hydrochloric acid. The resulting solution was subjected to HPLC, which showed the major peak of the product was identical with that of natural product, disodium salts of WS-1358A, disodium salts of 2-hydroxy-2-(hydroxycarbamoyl)-3-methylglutaric acid and the yield was 69%.

EXAMPLE 4

(1) 4-chloro-4,4-bis(ethoxycarbonyl)-3-methylbutyric acid (280.5 mg) was dissolved in dichloromethane (5 ml) and N-hydroxysuccinimide (115 mg) was added thereto. After the mixture was stirred for 1 hour at room temperature, dicyclohexylcarbodiimide (206 mg) was added at 0° C., and the resulting mixture was stirred overnight at room temperature. The mixture was filtered to remove N,N-dicyclohexylurea and the filtrate was concentrated to dryness to give 4-chloro-4,4-bis(ethoxycarbonyl)-3-methylbutyric acid succinimide ester. O-Benzylhydroxylamine.hydrochloride (192 mg) was dissolved in 1N sodium hydroxide (3 ml) and the solution was extracted with benzene (5 ml). The benzene extract was dried over magnesium sulfate to give anhydrous benzene solution, which was added to 4-chloro-4,4-bis(ethoxycarbonyl)-3-methylbutyric acid succinimide ester obtained in the above described operation. The resulting mixture was stirred overnight at room temperature. The reaction mixture was diluted with ethyl acetate (10 ml) and the solution was washed with 5% aqueous sodium bicarbonate, water, 0.1N hydrochloric acid and water successively. The organic solution was dried over magnesium sulfate and evaporated to give the crude product (380 mg), which was purified by silica gel column chromatography, eluted with a mixture of ethyl acetate and chloroform (5:95) to afford diethyl 2-chloro-2-[(2-benzyloxycarbamoyl-1-methyl)ethyl]malonate (345 mg) as an oil.

IR (CHCl$_3$, cm$^{-1}$): 3000, 1740, 1690, 1460 1365, 1300, 1250, 1095, 1035, $^1$H-NMR (CD$_3$OD): δ 6 7.4 (5H, m), 4.28 (2H, q, J=7 Hz), 4.27 (2H, q, J=7 Hz), 3.09 (1H, m), 2.45(1H, dd, J=14, 3 Hz), 2.00 (1H, dd, J=14, 10 Hz), 1.30 (3H, t, J=7 Hz), 1.29 (3H, t, J=7 Hz), 1.00 (3H, d, J=7 Hz).

(2) To a solution of diethyl 2-chloro-2-[(2-benzyloxycarbamoyl 1-methyl)ethyl]malonate (100 mg) in dioxane (10 ml) was added 10% palladium on carbon (30 mg) and the mixture was hydrogenated at room temperature and at atmospheric pressure for 1.5 hours. The reaction mixture was filtered and the filtrate was evaporated to give a residue (83 mg) containing a mixture of diethyl 2-chloro-2-[(hydroxycarbamoyl-1-methyl)ethyl]malonate and diethyl 2-[(hydroxycarbamoyl-1-methyl)ethyl]malonate. To this residue was added 1N sodium hydroxide (3 ml) and the resulting mixture was stirred for 5 hours at room temperature and then neutralized with 1N hydrochloric acid. The resulting solution was subjected to HPLC, which showed the major peak of the product was identical with that of natural product, WS-1358A, 2-hydroxy-2-(hydroxycarbamoyl)-3-methylglutaric acid and the yield was 52%. The solution was concentrated under reduced pressure to dryness to give a crude product containing disodium salts of 2-hydroxy-2-(hydroxycarbamoyl)-3-methylglutaric acid, $^1$H-NMR of which showed the major signals were identical with those of disodium salts of WS-1358A.

$^1$H NMR (200 MHz, D$_2$O) δ: 6: 2.77 (1H, m), 2.18 (1H, dd, J=13.5, 3 Hz), 1.96 (1H, dd, J=13.5, 11 Hz), 0.82 (3H, d, J=6.5 Hz).

EXAMPLE 5

(1) To a suspension of 60% sodium hydride (0.2 g) in dry benzene (30 ml) was added a solution of diethyl malonate (8 8 g) in benzene (30 ml) at 0° C. with stirring under nitrogen atmosphere. After gas evolution deceased, a solution of benzyl cinnamate (11.9 g) in benzene (30 ml) was added under nitrogen atmosphere. The mixture was stirred at 80° C. overnight. After cooled, the reaction mixture was poured into ice-water and the separated aqueous solution was neutralized with acetic acid (0.3 g). The benzene layer was washed with water and dried over magnesium sulfate. Removal of the solvent gave the oily residue (20.9 g). The residue was purified by column chromatography on silica gel (500 g), eluted with ethyl acetate-hexane (1:9) to afford benzyl 4,4-bis(ethoxycarbonyl)-3-phenylbutyrate (14.3 g) as an oil.

$^1$H-NMR (CDCl$_3$): 67 7.4 to 7.1 (10H, m), 4.95 (2H, s), 4.21 (2H, q, J=7 Hz), 3.92 (2H, q, J=7 Hz), 3.73 (1H, d, J=8 Hz), 2.92 (1H, dd, J=15, 5 Hz), 2.80 (1H, dd, J=15, 10 Hz), 1.25 (3H, t, J=7 Hz), 0.98 (3H, t, J=7 Hz).

EIMS: m/z 398 (M$^{30}$).

(2) To a solution of benzyl 4,4-bis(ethoxycarbonyl)-3-phenylbutyrate (3.98 g) in dioxane (50 ml) was added 10% palladium on carbon (0.5 g). The mixture was hydrogenated at 4 kgf/cm$^2$ for 1 hour. The reaction mixture was filtered and the filtrate was evaporated off to give 4,4-bis(ethoxycarbonyl)-3-phenylbutyric acid (2.7 g) as an oil.

$^1$H-NMR (CDCl$_3$): δ 6 7.3 to 7.15 (5H, m), 4.20 (2H, q, J=7 Hz), 3.92 (2H, q, J=7 Hz), 3.72 (1H, d, J=8 Hz), 2.90 (1H, dd, J=16,5 Hz), 2.78 (1H, dd, J=16, 10 Hz), 1.26 (3H, t, J=7 Hz), 1.0 (3H, t, J=7 Hz).

(3) 4,4-bis(Ethoxycarbonyl)-3-phenylbutyric acid (1.6 g) was dissolved in water (20 ml) and dioxane (30 ml). To this solution was added sodium hypochlorite solution (available chlorine: min 5%, ca 10 ml) while stirring the solution during a 30 minutes period until the pH rised to 7.0. After the mixture was stirred further 1 hour, the reaction mixture was acidified to pH 2 by addition of 1N hydrochloric acid and then extracted with ethyl acetate. The ethyl acetate extract was washed with water and evaporated to give a residue (1.8 g), which was purified by silica gel column chromatography, eluted with 5% isopropanol-benzene to afford 4-chloro-4,4-bis(ethoxycarbonyl)-3-phenylbutyric acid (1.57 g) as an oil.

$^1$H-NMR (CDCl$_3$): δ 6 7.4 to 7.2 (5H, m), 4.30 (3H, m), 4.00 (2H, m), 3.21 (1H, dd, J=16, 3.7 Hz), 3.05 (1H, dd, J=16, 9.3 Hz), 1.30 (3H, t, J=7 Hz), 1.12 (3H, t, J=7 Hz).

FABMS: m/z 343, 345 (M+H)$^+$ (4) To a solution of 4-chloro-4,4-bis(ethoxycarbonyl)-3-phenylbutyric acid (1.5 g) in dichloromethane (25 ml) was added N-hydroxysuccinimide (504 mg), and the mixture was stirred at room temperature for 1 hour. To the resulting solution was added dicyclohexyl carbodiimide (902 mg) at 0° C. and the mixture was stirred at 0° C. for 10 minutes and then at room temperature overnight. The reaction mixture was filtered, and the filtrate was concentrated to dryness under reduced pressure to give 4-chloro-4,4-bis(ethoxycarbonyl)-3-phenylbutyric acid succinimide ester (1.75 g) as an oil.

$^1$H NMR (CDCl$_3$): δ 7.45 to 7.25 (5H, m), 4.33 (3H, m), 4.02 (2H, m), 3.55 (1H, dd, J=16, 3.5 Hz), 3.34 (1H, dd, J=16, 9 Hz), 2.75 (4H, s), 1.32 (3H, t, J=7 Hz), 1.12 (3H, t, J=7 Hz). (5) To a solution of hydroxylamine hydrochloride (358 mg) in water (5 ml) was added 1N aqueous sodium hydroxide (6.45 ml) at 0° C. with stirring. The resulting solution was added to a solution of 4-chloro-4,4-bis(ethoxycarbonyl)-3-phenylbutyric acid succinimide ester (1.75 g) in ethanol (15 ml) at 0° C. The mixture was stirred at room temperature overnight. The reaction mixture (pH 7) was extracted with ethyl acetate and the extract was washed with water, dried over magnesium sulfate and then evaporated to give a residue (1.2 g), which was purified by silica gel column chromatography, eluted with a mixture of methanol and chloroform (5:95) to afford diethyl 2-chloro-2-[(2-hydroxycarbamoyl-1-phenyl)ethyl]malonate (670 mg) as an oil.

$^1$H NMR (CD$_3$OD): δ 7.4 to 7.25 (5H, m), 4.41 to 4.20 (3H, m), 4.00 (2H, m), 2.93 (1H, dd, J=15, 4 Hz), 2.80 (1H, dd, J=15, 10 Hz), 1.28 (3H, t, J=7 Hz), 1.11 (3H, t, J=7 Hz).

FABMS: m/z 358, 360 (M+H)+. (6) To diethyl 2-chloro-2-[(2-hydroxycarbamoyl-1phenyl)ethyl]malonate (50 mg) was added 1N sodium hydroxide (1.2 ml), and the mixture was stirred for 2 hours at room temperature. The resulting solution was neutralized by adding Dowex 50 W×2 (H+) (ca. 2 ml) and the resin was filtered off. The filtrate was evaporated to give 2-hydroxy-2-(hydroxycarbamoyl)-3-phenylglutaric acid (39.6 mg) as a powder.

$^1$H NMR (D$_2$O): δ 7.5 to 7.25 (5H, m), 3.98 (1H, dd, J=11, 3.6 Hz), 2.72 (1H, dd, J=14, 11 Hz), 2.50 (1H, dd, J=14, 3.6 Hz).

$^{13}$C NMR (D$_2$O): δ 183.4, 176.4, 172.7, 141.6, 132.3, 132.3, 130.7, 130.7, 129.8, 85.7, 49.9, 41.0.

FABMS: m/z 329 (M+2 Na)+.

We claim:

1. An antibacterial composition comprising a compound of the formula:

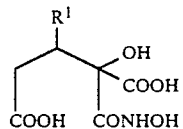

wherein R$^1$ is hydrogen, lower alkyl or aryl, or pharmaceutically acceptable salt thereof and pharmaceutically acceptable carrier(s).

2. The antibacterial composition of claim 1, in which in the compound of formula (I) R$^1$ is methyl.

3. An antibacterial composition comprising a carbapenem antibiotic or pharmaceutically acceptable salt thereof and a compound of the formula:

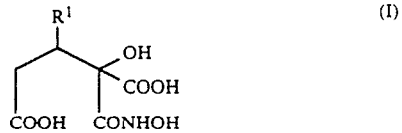

wherein R$^1$ is hydrogen, lower alkyl or aryl, or pharmaceutically acceptable salt thereof and pharmaceutically acceptable carrier(s).

4. A substantially pure compound of the formula:

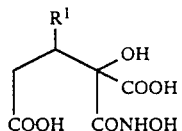

wherein R$^1$ is hydrogen, lower alkyl or aryl, or pharmaceutically acceptable salt thereof.

5. The compound of claim 4, in which R$^1$ is methyl.

* * * * *